(12) United States Patent
Alpert et al.

(10) Patent No.: US 9,795,776 B2
(45) Date of Patent: Oct. 24, 2017

(54) SYSTEM AND METHOD FOR JOINT INTEGRITY DETECTION

(71) Applicant: CareFusion 303, Inc., San Diego, CA (US)

(72) Inventors: Robert Steven Alpert, Escondido, CA (US); Lisa Davis, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 145 days.

(21) Appl. No.: 14/451,373

(22) Filed: Aug. 4, 2014

(65) Prior Publication Data

US 2014/0339814 A1 Nov. 20, 2014

Related U.S. Application Data

(63) Continuation of application No. 13/225,262, filed on Sep. 2, 2011, now Pat. No. 8,795,452.

(51) Int. Cl.
*B32B 41/00* (2006.01)
*A61M 39/10* (2006.01)
(Continued)

(52) U.S. Cl.
CPC ........ *A61M 39/10* (2013.01); *A61M 5/16831* (2013.01); *A61M 5/5086* (2013.01);
(Continued)

(58) Field of Classification Search
CPC .............. A61M 39/10; A61M 39/1011; A61M 25/0009; A61M 5/5086; A61M 5/16831; A61M 39/18; A61M 39/08; A61M 2039/1005; A61M 2205/15; B29C 66/1142; B29C 66/1122; B29C 65/48; B29C 65/00; B29C 66/63; B29C 66/96; B29C 65/7802; B29C 66/43; B29C 66/534; B29C 66/12841; B29C 66/1222; B29C 66/5224;
(Continued)

(56) References Cited

U.S. PATENT DOCUMENTS 4,693,710 A 9/1987 McCool
5,782,810 A 7/1998 O'Donnell
(Continued)

FOREIGN PATENT DOCUMENTS

EP 0075039 B1 12/1986
WO 2011009885 A1 1/2011

OTHER PUBLICATIONS

International Search Report and Written Opinion for PCT/US2012/051620 mailed Jan. 21, 2013.

*Primary Examiner* — Michael N Orlando
*Assistant Examiner* — Joshel Rivera
(74) *Attorney, Agent, or Firm* — McDermott Will & Emery LLP (57) ABSTRACT

An inspectable joint in a medical device is disclosed that includes at least one medical-grade tube having an end, a medical-grade fitting having at least one joining surface configured to accept the end of the tube, and a joining material disposed between the tube and the joining surface. The joining material includes a first component configured to couple the tube to the fitting and a second component configured to provide observable evidence of the presence of the joining material between the tube and the joining surface.

19 Claims, 5 Drawing Sheets

(51) Int. Cl.
- A61M 5/168 (2006.01)
- A61M 5/50 (2006.01)
- A61M 39/08 (2006.01)
- A61M 39/18 (2006.01)
- B29C 65/82 (2006.01)
- B29C 65/00 (2006.01)
- A61M 25/00 (2006.01)
- B29C 65/78 (2006.01)
- B29C 65/48 (2006.01)

(52) U.S. Cl.
CPC ........ *A61M 25/0009* (2013.01); *A61M 39/08* (2013.01); *A61M 39/1011* (2013.01); *A61M 39/18* (2013.01); *B29C 65/00* (2013.01); *B29C 65/48* (2013.01); *B29C 65/7802* (2013.01); *B29C 65/8253* (2013.01); *B29C 66/1122* (2013.01); *B29C 66/1142* (2013.01); *B29C 66/1222* (2013.01); *B29C 66/1224* (2013.01); *B29C 66/1282* (2013.01); *B29C 66/12841* (2013.01); *B29C 66/305* (2013.01); *B29C 66/342* (2013.01); *B29C 66/43* (2013.01); *B29C 66/5221* (2013.01); *B29C 66/5224* (2013.01); *B29C 66/5229* (2013.01); *B29C 66/534* (2013.01); *B29C 66/5344* (2013.01); *B29C 66/612* (2013.01); *B29C 66/63* (2013.01); *B29C 66/73365* (2013.01); *B29C 66/96* (2013.01); *A61M 2039/1005* (2013.01); *A61M 2205/15* (2013.01); *B29C 65/485* (2013.01); *B29C 65/4845* (2013.01); *B29C 65/4895* (2013.01); *B29C 65/8284* (2013.01); *Y10T 156/10* (2015.01); *Y10T 156/1038* (2015.01)

(58) Field of Classification Search
CPC ............ B29C 66/1282; B29C 66/5221; B29C 66/5229; B29C 66/73365; B29C 66/1224; B29C 66/5344; B29C 66/305; B29C 65/8253; B29C 66/342; B29C 65/4845; B29C 65/4895; B29C 65/485; B29C 65/8284; Y10T 156/1038; Y10T 156/10
USPC ............ 156/60, 64, 67, 272.2, 272.8, 379.6; 604/523, 533; 600/435; 29/428
See application file for complete search history.

(56) References Cited

U.S. PATENT DOCUMENTS

| | | |
|---|---|---|
| 6,764,710 B2 | 7/2004 | Merdan et al. |
| 2003/0135197 A1* | 7/2003 | Wang ................ A61M 25/0009 604/523 |
| 2003/0226631 A1 | 12/2003 | Sterud et al. |
| 2004/0059301 A1 | 3/2004 | Matsumoto |

* cited by examiner

SYSTEM AND METHOD FOR JOINT INTEGRITY DETECTION

RELATED APPLICATIONS

This application is a continuation of U.S. application Ser. No. 13/225,262, filed Sep. 2, 2011, entitled, "SYSTEM AND METHOD FOR JOINT INTEGRITY DETECTION," the disclosure of which is incorporated herein by reference in its entirety.

BACKGROUND

Field

The present disclosure is related to the inspection of bonded joints and, in particular, bonded joints between tubes and fittings in medical systems.

Description of the Related Art

Patients in hospitals are often provided with medical fluids that are administered through an intravenous (IV) infusion using assemblies of tubes and fittings commonly referred to as "IV sets." IV sets are produced in a variety of configurations with various types of needleless access ports, check valves, drip chambers, and other fittings connected by lengths of medical tubing. Each of the connections between a tube and a fitting, sometimes referred to as a "joint" or an "engagement," must be bonded. A defect, such as a void or leakage path, in any bond or the failure to bond a particular joint in an IV set may lead to leakage, air being introduced into the line, or other hazard and the resultant need for the caregiver to replace the entire IV set. As a single manufacturer may produce in excess of 100 million IV sets, with an average of 10 joints per IV set, the number of potential failure sites for that manufacturer alone may exceed 1 billion.

One method of inspecting the joints of IV sets is to pressurize the IV set and measure the rate of pressure decay. This is a relatively slow and costly process that requires significant capital equipment.

SUMMARY

It is desirable to provide a way to perform a reliable inspection of joint integrity that is fast and inexpensive. The apparatus and methods disclosed herein provide inspectable joints that, in certain embodiments, can be visually inspected. In other embodiments, other automatic inspection methods may be used to verify the presence of a good joint between a tube and a fitting. A "good" joint is a joint without a void or a leakage path.

In certain embodiments, an inspectable joint in a medical device is disclosed. The inspectable joint includes at least one medical-grade tube comprising an end, a medical-grade fitting having at least one joining surface configured to accept the end of the tube; and a joining material disposed between the tube and the joining surface. The joining material has a first component configured to couple the tube to the fitting and a second component configured to provide observable evidence of the presence of the joining material between the tube and the joining surface.

In certain embodiments, an IV set is disclosed that includes at least one medical-grade tube having an end, a medical-grade fitting having at least one joining surface configured to accept the end of the tube; and a joining material disposed between the tube and the joining surface. The joining material has a first component configured to couple the tube to the fitting and a second component configured to provide observable evidence of the presence of the joining material.

In certain embodiments, a method of inspecting a joint in a medical device is disclosed. The method includes the step of applying a joining material comprising a first component and a second component to at least one of an end of a medical-grade tube and a joining surface of a medical-grade fitting. The joining surface is configured to accept the tube end. The first component is configured to couple the tube to the fitting and the second component is configured to provide observable evidence of the presence of the joining material. The method also includes the steps of assembling the joint by accepting the tube end onto the joining surface of the fitting, observing a bonding area between the tube and the fitting; and determining how much of the bonding area has the joining material disposed between the tube and the fitting.

In certain embodiments, an inspectable joint is disclosed that includes at least one tube having an end, a fitting having at least one joining surface configured to accept the tube end, and a bonding agent coupled between the tube end and the joining surface. The bonding agent includes an adhesion component configured to couple the tube to the fitting and a detectable component.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of an inspectable joint and methods of inspecting such joints. The description is presented in the context of joints between medical tubing and fittings as are commonly used in IV sets. It will be obvious to those of ordinary skill in the art that the same design principles and methods may be used in other environments, such as automated food packaging or industrial systems, where fluids are transferred through plastic lines that are bonded to fittings. The disclosed embodiments are illustrative only and do not limit the scope of the disclosure.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1A:
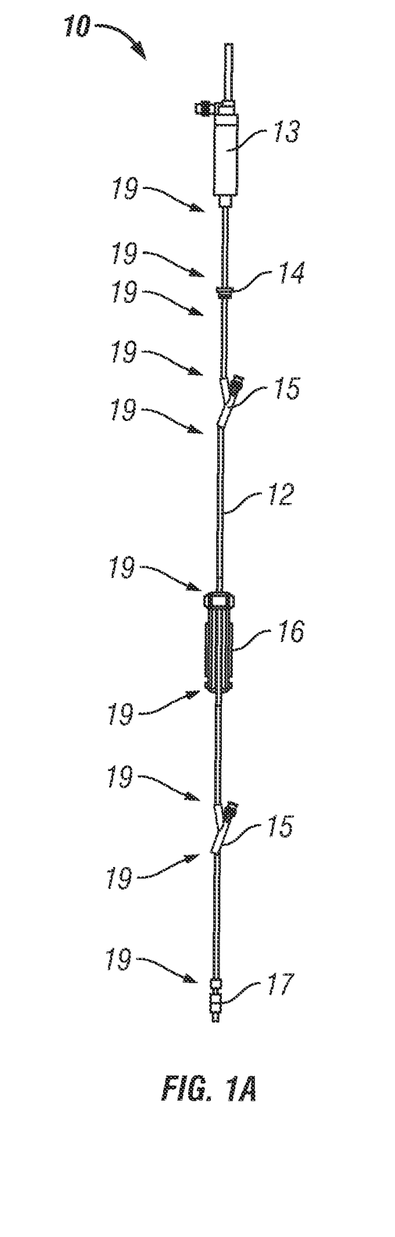
FIG. 1A depicts an IV set according to certain aspects of the present disclosure.

FIG. 1A depicts an IV set 10 according to certain aspects of the present disclosure. The IV set 10 includes a drip chamber 13 integrated with a bag spike or other connector suitable for connection to an IV bag (not shown). The IV set 10 also includes a check valve 14, two needleless access ports 15, a pumping segment 16 configured to be coupled to an IV pump (not shown), and a needleless fitting 17 for connection to an infusion needle (not shown) or other infusion apparatus. Each of these items are connected to one or more lengths of medical-grade tubing 12 by a joint 19. It can be seen that this example IV set has ten joints 19.

Figure 1B:
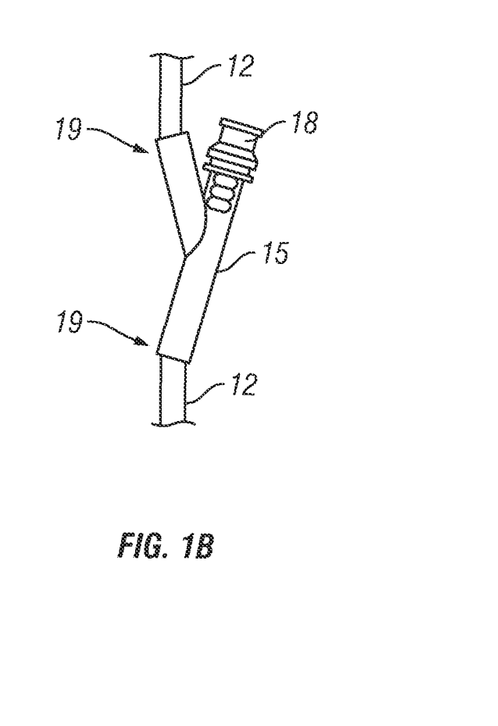
FIG. 1B is a close-up of a needleless access port from the IV set of FIG. 1A according to certain aspects of the present disclosure.

FIG. 1B is a close-up of a needleless access port 15 from the IV set 10 of FIG. 1A according to certain aspects of the present disclosure. The fitting 15 includes a needleless access valve 18 and two joints 19 between lengths of tube 12 and the fitting 15.

Figure 2A:
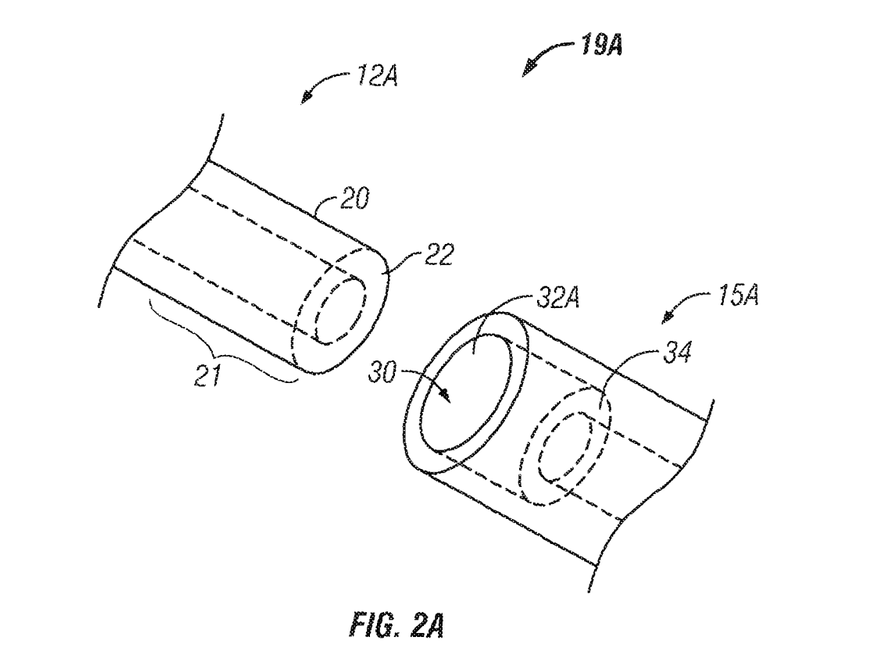
FIGS. 2A and 2B are exemplary inspectable joints according to certain aspects of the present disclosure.
Figure 2B:
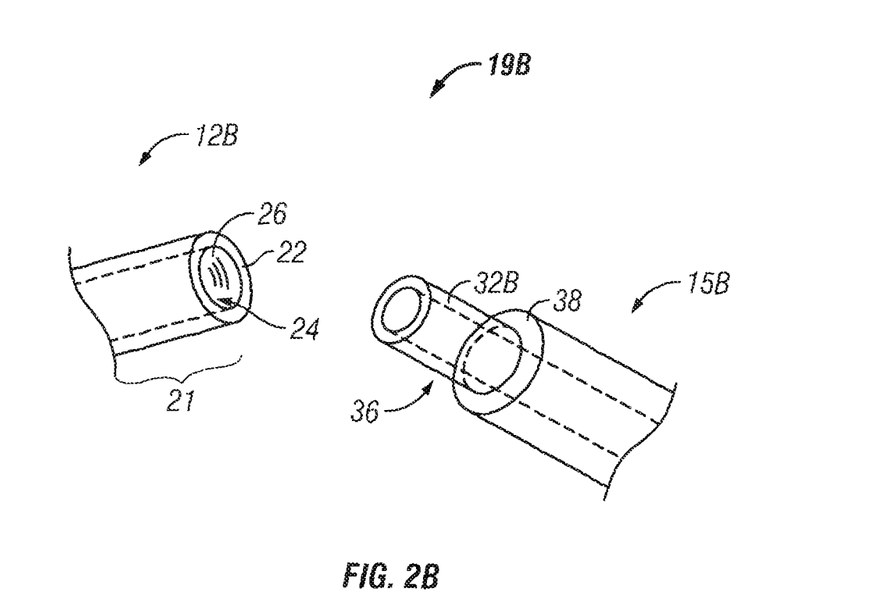

FIGS. 2A and 2B are exemplary inspectable joints 19A and 19B according to certain aspects of the present disclosure. FIG. 2A depicts a configuration wherein tube 12A fits into a pocket 30 such that a portion 21 of the outer surface 20 of tube 12A overlaps the interior wall 32A of pocket 30. Tube 12A is typically inserted into pocket 30 until the end 22 of tube 12A contacts the bottom 34 of the pocket 30. The area of overlap, also referred to as the bonding area of the joint 19, is coincident with the interior wall 32A in the joint 19 of FIG. 2A.

FIG. 2B illustrates another embodiment of a joint 19B wherein tube 12B is configured to fit over a tubular post 36. Portion 21 of the interior surface 26 of the tube bore 24 overlaps the exterior surface 32B of the tubular post 36. The end 22 of tube 12B is typically in contact with the surface 38 of the fitting 15B. In all disclosures herein of inspectable joints and inspection equipment and methods, a disclosure related to the embodiment of FIG. 2A is applicable to the embodiment of FIG. 2B with suitable rearrangement and reconfiguration of components.

In general, for joints between a tube 12 and a fitting 15, a joining material (not shown in FIG. 2A or 2B) is applied to one of the overlapping surfaces, for example 20/32A or 26/32B, so that the joining compound will sealingly couple the tube 12 to the fitting 15. In certain embodiments, the joining material is an adhesive that bonds to both of the overlapping surfaces, with the adhesive remaining in place after the bond is formed. In certain embodiments, the joining material is a solvent that causes the overlapping surfaces to bond directly to each other, wherein the solvent then evaporates or otherwise dissipates from the area of the joint 19. In certain embodiments, the joining material requires exposure to a curing environment, for example exposure to ultraviolet light. In certain embodiments, the joining material will cure after a certain amount of time elapses after the joint 19 is assembled. In certain embodiments, the joining material is applied to one of the overlapping surfaces of the joint 19 and an activator (not shown in FIGS. 2A and 2B) is applied to the other of the overlapping surfaces such that the activator comes into contact with the joining material upon assembly of the joint 19, thereby initiating the cure of the joining material.

In certain embodiments, the tube 12 and the pocket 30 of fitting 15 are both round. In certain embodiments, a pair of tubes (not shown) may be attached to each other in parallel and the pocket shaped to match the profile of the paired tubes. In certain embodiments, the shape of tube 12 and pocket 30 have an oval or other non-circular profile. In certain embodiments, fitting 15 is a part of a larger apparatus, such as an integrated IV bag (not shown). In certain embodiments, the tube 12 and fitting 15 are made of medical-grade materials, i.e. approved for contact with the human body or fluids that will be introduced into the human body. In certain embodiments, a tube 12 and fitting 15 may be used for non-medical purposes and, therefore, may include non-medical-grade materials.

Figure 2C:
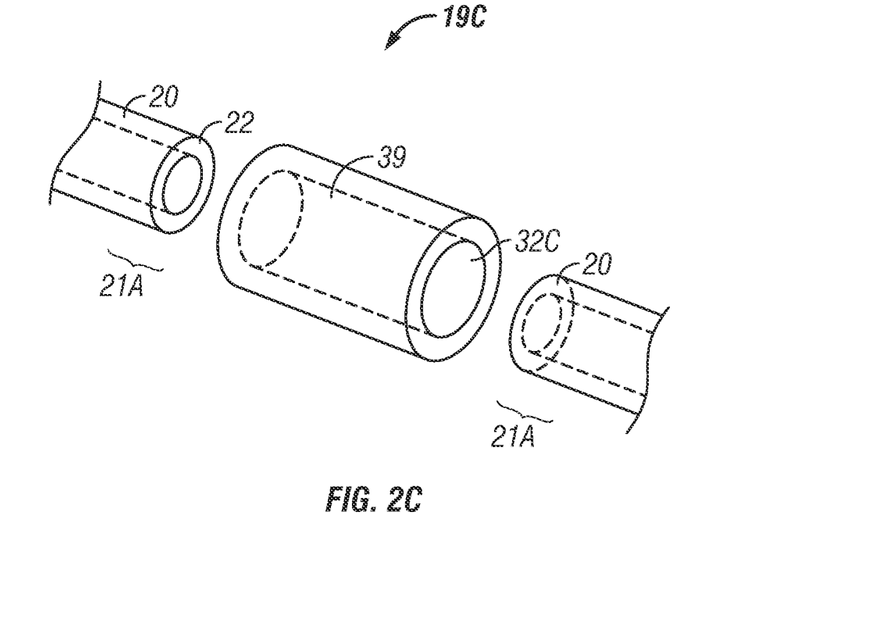
FIG. 2C depicts an embodiment of a tube-to-tube inspectable joint according to certain aspects of the present disclosure.

FIG. 2C depicts an embodiment of a tube-to-tube inspectable joint 19C according to certain aspects of the present disclosure. In this embodiment, two tubes 20 are joined together by a sleeve 39 that fits over the exterior of the tubes 20. The sleeve 39 has a bonding surface 32C on the interior surface. Each of the tubes 20 has a region 21A that will overlap the bonding area 32C when the ends of tubes 20 are inserted into the sleeve 39. In certain embodiments, the ends 22 of tubes 20 will contact each other when fully inserted.

Figure 2D:
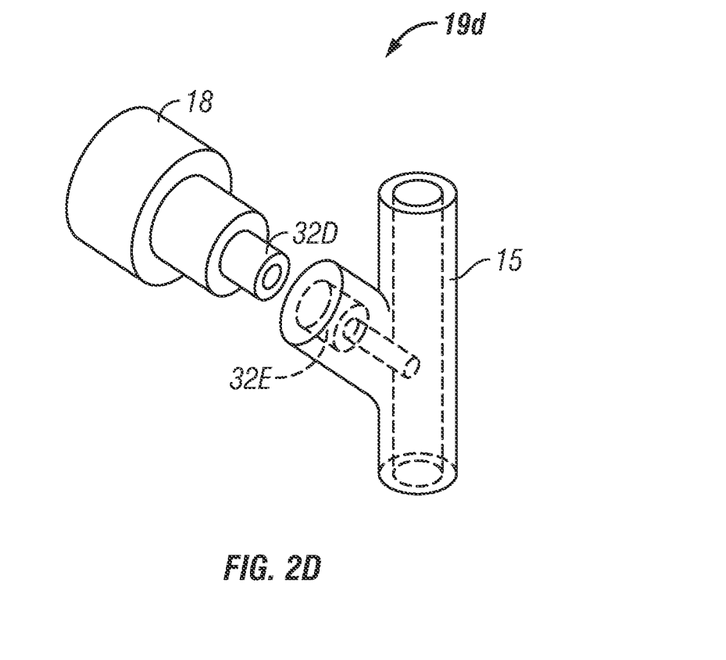
FIG. 2D depicts an embodiment of a component-to-component inspectable joint according to certain aspects of the present disclosure.

FIG. 2D depicts an embodiment of a component-to-component inspectable joint 19D according to certain aspects of the present disclosure. In this example, a needleless access port 18 is to be coupled to a Y-fitting 15. In certain embodiments, both components 15, 18 are made from materials that are rigid compared to the flexible lines 20. In the embodiment of FIG. 2D, the needleless access port 18 has a bonding area 32D that will overlap with the bonding area 32E of the Y-fitting 15 when assembled. In certain embodiments, other surfaces of the two components are configured to be bonded to each other.

Figure 3A:
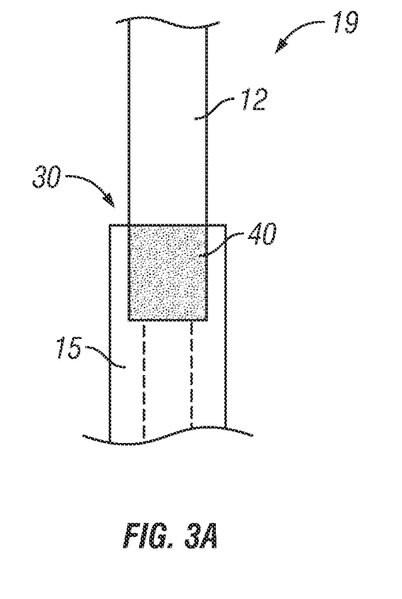
FIG. 3A illustrates an example of a properly bonded inspectable joint according to certain aspects of the present disclosure.

FIG. 3A illustrates an example of a properly bonded inspectable joint 19 according to certain aspects of the present disclosure. In this example, a tube 12 is inserted into a pocket 30 of a fitting 15. A joining material 40 has been applied to one of the overlapping surfaces of the tube 12 and fitting 15 and is shown in FIG. 3A as fully covering the overlapping surfaces. In certain embodiments, the joining material 40 is colored such that an operator or a machine-vision system can visually inspect the joint 19 by observing the bonding area, i.e. the area of overlap between the tube 12 and the fitting 15 of the joint 19 and determining how much of the bonding area is covered by the joining material 40. The presence of joining material 40 in a given region between the tube and fitting is considered an acceptable indication that the region is bonded to both the tube 12 and fitting 15 as the gap between the tube 12 and fitting 15 is usually sufficient only to provide a thickness of joining material 40, i.e. a "bond line," sufficient to form a good bond in accordance with normal practice for the design of joints for the joining material. While the illustration of FIG. 3A is a two dimensional view of a single side of the joint 19, it will be apparent to those skilled in the art that the joint is a three dimensional surface and must be inspected around the circumference of the joint 19 using the same criteria as described above to make a complete inspection.

In certain embodiments, the joining material 40 includes a first component that is configured to bond to the tube 12 and fitting 15 and a second component configured to color the joining material 40. An exemplary first component is acrylic. This second component may be a liquid dye or a finely ground inert opaque solid. In certain embodiments, the second component may be finely ground pieces of a colored form of the same material that forms the fitting 15, such as polyester. In certain embodiments, the second component is a material that responds to non-visible radiation, such as ultraviolet light, and thereby become visible during or after such exposure. In certain embodiments, the second component fluoresces, i.e. glows in the visible spectrum, during and after exposure to non-visible radiation. In certain embodiments, the joining material 40 has a color when in the uncured state, i.e. when first applied to either the tube 12 or fitting 15, and then fades to a substantially transparent state when the joining material 40 cures. In certain embodiments, the joining material 40 has a first color when in the uncured state, i.e. when first applied to either the tube 12 or fitting 15, and then changes to a different second color when the joining material 40 cures. In certain embodiments, the joining material 40 has a color when first applied to either the tube 12 or fitting 15, and then fades to a substantially transparent state when the joint 19 undergoes exposure to a sterilizing environment, i.e. exposure to high temperature or to a sterilizing gas. In certain embodiments, the joining material 40 has a first color when first applied to either the tube 12 or fitting 15, and then changes to a second different color when the joint 19 undergoes exposure to a sterilizing environment, i.e. exposure to high temperature or to a sterilizing gas.

In order to facilitate a visual inspection of the presence of the joining material 40 between the tube 12 and fitting 15 in the example of FIG. 3A, the fitting 15 must be translucent to a degree sufficient to differentiate between the presence and the absence of the joining material 40. In certain embodiments, the fitting 15 is substantially transparent. Within this disclosure, the phrase "at least translucent" indicates that the material transmits light to a degree that is within an inclusive range between partial transmission, i.e. some of the light is blocked, and complete transmission, i.e. transparent, and include such optical characterizations as "frosted," "semi-opaque," "semitransparent," and "milky." If the joint 19 is configured as illustrated in FIG. 2B, wherein the tube 12 fits over the fitting 15, then it is the tube 12 that is either translucent or transparent. In certain embodiments, the interior element of the joint 19, i.e. the tube 12 of the joint 19 shown in FIG. 3A, is not transparent so that it is easier to determine whether there is joining material on the side of the interior element towards the observer.

Figure 3B:
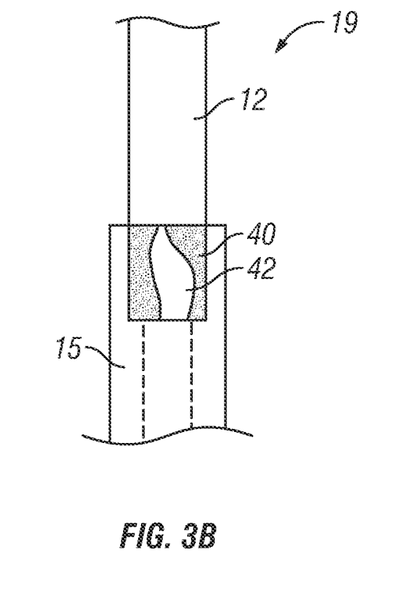
FIG. 3B illustrates an inspectable joint with an example void according to certain aspects of the present disclosure.

FIG. 3B illustrates an inspectable joint 19 with a void 42 according to certain aspects of the present disclosure. In this example, the joining material 40 does not fill the entire bonding area between the tube 12 and fitting 15, leaving a void 42. In the example of FIG. 3B, the void 42 extends from the open edge of the joint 19 to the interior edge of the joint 19, thereby forming a leakage path. In certain embodiments, the void 42 does not contact one or both edges of the joint 19 and forms an isolated bubble (not shown) within the bond area. In certain embodiments, bubbles of a certain size or area are allowable as long as they do not contact an edge. In certain embodiments, bubbles are not acceptable if larger than a certain size.

Figure 4:
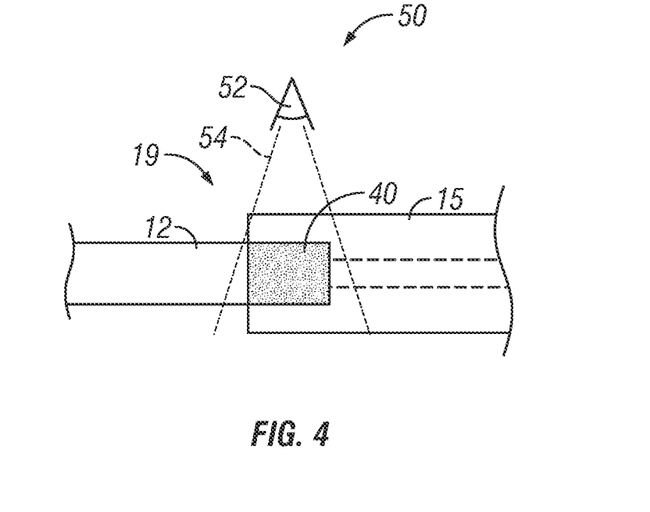
FIG. 4 schematically illustrates an exemplary optical inspection system according to certain aspects of the present disclosure.

FIG. 4 illustrates an exemplary optical inspection system 50 according to certain aspects of the present disclosure. A visual inspection sensor 52 is oriented so as to observe the region 54 wherein a properly formed joint 19 between tube 12 and fitting 15 will have joining material 40 disposed between the tube 12 and fitting 15. In certain embodiments, the visual inspection sensor 52 is connected to a tester (not shown in FIG. 4) comprising a processor that is configured to interpret the output of the visual inspection sensor 52 and determine how much of the bonding area has the joining material 40 disposed between the tube 12 and the fitting 15. In certain embodiments, the joint 19 under inspection is exposed to non-visible light (not shown in FIG. 4) while being inspected so as to cause the joining material 40 to be visible. In certain embodiments, the inspection is performed by a person in place of the visual inspection sensor 52. In certain embodiments, the system 50 includes multiple sensors 52 so as to simultaneously inspect all sides of the joint 19.

Figure 5:
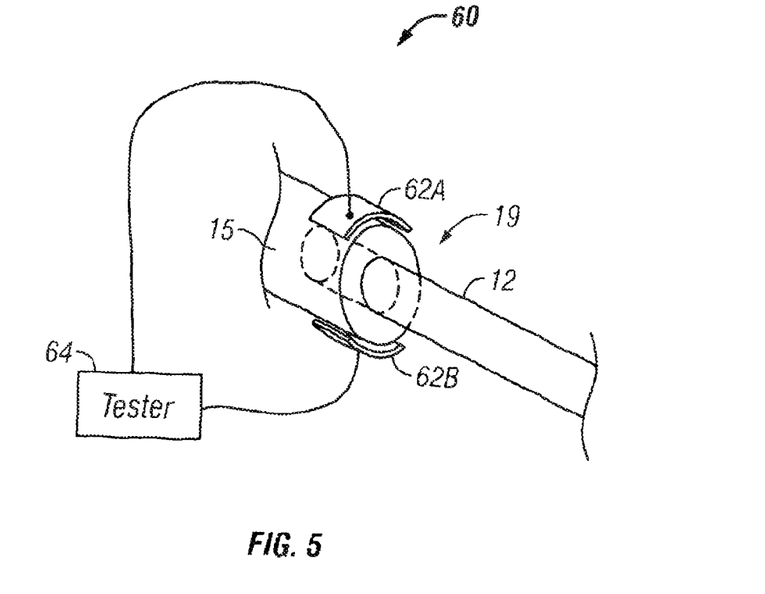
FIGS. 5 and 6 schematically depict exemplary inspection systems according to certain aspects of the present disclosure.
Figure 6:
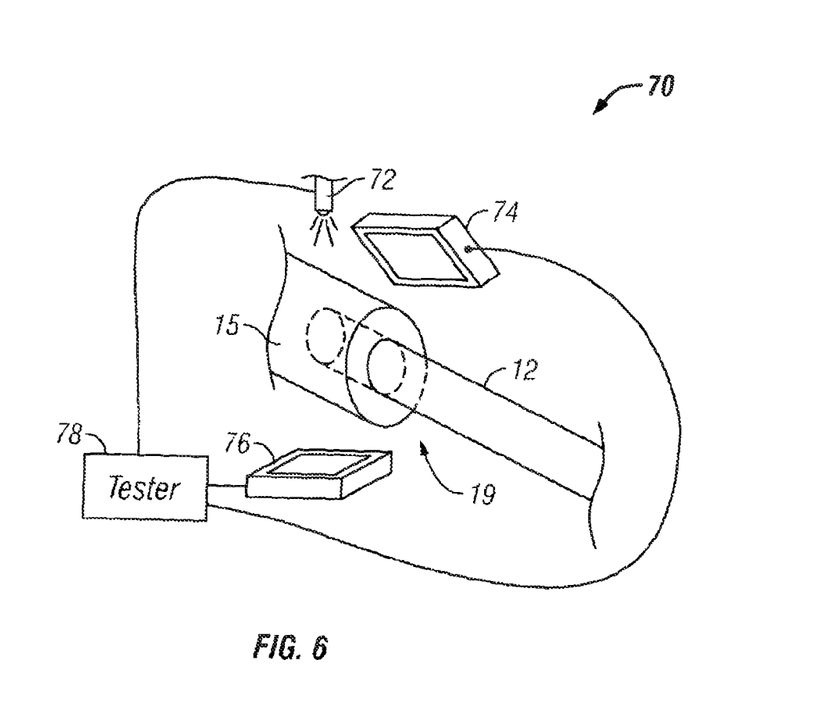

FIGS. 5 and 6 depict exemplary inspection systems 60 and 70 according to certain aspects of the present disclosure. FIG. 5 depicts an inspection system 60 configured to measure at least one of the resistance, impedance, and capacitance of the joint 19 according to standard measurement protocols for these characteristics as known to those of skill in the art. In certain embodiments, the joining material 40 includes a component that has a property, for example conductivity, that is sufficiently different from the materials used in the tube 12 and fitting 15 so as to allow the system 70 to differentiate a joint that has an appropriate amount of joining material 40 from a joint that has a lesser amount of the joining material 40. In certain embodiments, electrodes 62A and 62B contact the fitting 15. In certain embodiments, the electrodes 62A, 62B are not in contact with the fitting 15. The electrodes 62A, 62B are coupled to a tester 64 adapted to provide the proper stimulation signal, detect the appropriate response signal, and interpret the detected signal to determine whether the joining material is present in the bonding area of joint 19. In certain embodiments, one of the electrodes 62A, 62B is replaced with a coil (not shown) so as to create a magnetic field adapted to detect the presence of a joining material that includes a component having detectable magnetic properties.

FIG. 6 depicts an inspection system 70 configured to measure at least one of a transmitted or reflected radiation measurement of the joint 19. Radiation as considered within the scope of this disclosure includes visible light, infrared and ultraviolet radiation, x-ray radiation, and other types of radiation known to those of skill in the art to provide images of internal and/or external structures. In certain embodiments, the joining material 40 includes a component that is less transparent to the radiation type to be used in the inspection system 70 than the materials of the fitting 15 or tube 12 so as to allow the system 70 to differentiate the joining material 40 from the surrounding structure. Radiation is provided by an emitter 72 that is coupled to a tester 78. In certain embodiments, at least a portion of the radiation from emitter 72 passes through the joint 19 and is detected by receiver 76. In certain embodiments, at least a portion of the radiation from emitter 72 is reflected by the joint 19 and detected by receiver 74. Tester 78 is adapted to control the emitter 72 as well as receive and interpret the detected signals from receivers 74 and 76 as installed in the inspection system 70.

The disclosed inspectable joint provides an elegant solution to the need to provide a reliable and low-cost method of inspecting the bonded joints in systems such as medical IV sets. The inclusion of a colorant or other detectable component in the joining material allows the automated inspection of joint integrity and, in certain embodiments, improves the accuracy and reliability of a manual inspection process. The disclosed optical inspection system provides a quick and reliable alternative to the existing pressure-decay inspection technique. The inclusion of other detectable materials, such as a magnetic material, in the joining material provides other methods of inspecting the joint.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. An inspectable joint in a medical device, the inspectable joint comprising:
at least one medical-grade tube comprising an end;
a medical-grade fitting comprising at least one joining surface configured to accept the end of the tube; and
a joining material disposed between the tube and the joining surface, the joining material comprising: (i) a first component configured to bond the tube to the fitting; and (ii) a second component configured to provide observable evidence of the presence of the joining material that is between the tube and the joining surface; at least a portion of the first component contacts at least a portion of the second component when the tube end is accepted by the joining surface, and at least one of the portions of the first and second components that contacts the other of the first and second components has an initial first color;
wherein the at least a portion of one of the first and second components changes color to a second color upon contact with the portion of the other of the first and second components, and wherein the tube is separated from the joining surface by a gap, and the joining material extends around a circumference of the joint between the tube and the joining surface.

2. The inspectable joint of claim 1, wherein the joining surface of the fitting is a pocket configured to accept the tube end into the pocket and at least a portion of the fitting is at least translucent.

3. The inspectable joint of claim 1, wherein the joining surface of the fitting is a tubular post configured to accept the tube end over the tubular post and at least a portion of the tube over the joining surface is at least translucent.

4. The inspectable joint of claim 1, wherein the joining material is only observable during or after exposure to non-visible radiation.

5. The inspectable joint of claim 4, wherein the joining material fluoresces during or after exposure to non-visible radiation.

6. The inspectable joint of claim 1, wherein the first component comprises an adhesive configured to bond to the tube and the fitting; and wherein the adhesive is configured to cure and thereby form a permanent bond with the tube and the fitting.

7. The inspectable joint of claim 1, wherein the first component comprises a solvent configured to cause the tube to bond directly with the fitting; and wherein the solvent dissipates after a first determined period of time has elapsed after the time of application.

8. The inspectable joint of claim 1, wherein the second component is configured such that the joining material is colored when the joining material is initially applied to at least one of the tube and the fitting; and such that the joining material becomes substantially transparent after a second determined period of time has elapsed after the time of application.

9. The inspectable joint of claim 1, wherein the second component is configured such that the joining material is colored when the joining material is initially applied to at least one of the tube and the fitting; and the joining material becomes substantially transparent after the assembled joint is exposed to a sterilizing environment.

10. An intravenous set comprising:
at least one medical-grade tube comprising an end;
a medical-grade fitting comprising at least one joining surface configured to accept the end of the tube; and
a joining material disposed between the tube and the joining surface, the joining material comprising: (i) a first component configured to bond the tube to the fitting; and (ii) a second component configured to provide observable evidence of the presence of the joining material; wherein at least a portion of one of the first and second components has an initial first color and contacts at least a portion of the other of the first and second components;
wherein the at least a portion of one of the first and second components changes color to a second color upon contact with the portion of the other of the first and second components when the tube end is accepted by the joining surface, and wherein the tube is separated from the joining surface by a gap, and the joining material extends around a circumference of the joint between the tube and the joining surface.

11. The intravenous set of claim 10, wherein the first component comprises an adhesive configured to bond to the tube and the fitting; and wherein the adhesive is configured to cure and thereby form a permanent bond with the tube and the fitting.

12. The intravenous set of claim 10, wherein the first component comprises a solvent configured to cause the tube to bond directly with the fitting; and wherein the solvent dissipates after a first determined period of time has elapsed after the time of application.

13. The intravenous set of claim 10, wherein the second component is configured such that the joining material is colored when the joining material is initially applied to at least one of the tube and the fitting; and such that the joining material becomes substantially transparent after a second determined period of time has elapsed after the time of application.

14. The intravenous set of claim 10, wherein the second component is configured such that the joining material is colored when the joining material is initially applied to at least one of the tube and the fitting; and the joining material becomes substantially transparent after the assembled joint is exposed to a sterilizing environment.

15. An inspectable joint comprising:
  at least one tube comprising an end;
  a fitting comprising at least one joining surface configured to accept the tube end; and
  a bonding agent coupled between the tube end and the joining surface, the bonding agent comprising: (i) an adhesion component configured to bond the tube to the fitting; and (ii) a detectable component configured to provide evidence of the presence of the bonding agent between the tube and the joining surface; at least a portion of one of the adhesion and detectable components has an initial first color and contacts at least a portion of the other of the adhesion and detectable components when the tube end is accepted by the joining surface;
  wherein the at least a portion of one of the adhesion and detectable components changes color to a second color upon contact with the portion of the other of the adhesion and detectable components such that a void between the tube end and joining surface is identifiable, and wherein the tube is separated from the joining surface by a gap, and the bonding agent extends around a circumference of the joint between the tube and the joining surface.

16. The inspectable joint of claim 15, wherein the detectable component can be detected by an optical test.

17. The inspectable joint of claim 15, wherein the detectable component can be detected by at least one of the set of a resistance test, an impedance test, and a capacitance test.

18. The inspectable joint of claim 15, wherein the detectable component can be detected by a magnetic test.

19. The inspectable joint of claim 15, wherein the detectable component can be detected by at least one of the set of a transmissive radiation test and a reflected radiation test.

* * * * *